US012596869B2

(12) United States Patent
Cheng et al.

(10) Patent No.: US 12,596,869 B2
(45) Date of Patent: Apr. 7, 2026

(54) DETECTING ARTIFICIAL INTELLIGENCE GENERATED TEXT

(71) Applicant: NEC Laboratories America, Inc., Princeton, NJ (US)

(72) Inventors: Wei Cheng, Princeton Junction, NJ (US); Haifeng Chen, West Windsor, NJ (US); Xianjun Yang, Santa Barbara, CA (US)

(73) Assignee: NEC Corporation, Tokyo (JP)

( * ) Notice: Subject to any disclaimer, the term of this patent is extended or adjusted under 35 U.S.C. 154(b) by 154 days.

(21) Appl. No.: 18/654,795

(22) Filed: May 3, 2024

(65) Prior Publication Data

US 2024/0378380 A1 Nov. 14, 2024

Related U.S. Application Data

(60) Provisional application No. 63/465,063, filed on May 9, 2023.

(51) Int. Cl.
*G06F 40/20* (2020.01)
*G16H 10/60* (2018.01)
*G16H 50/20* (2018.01)
*G16H 50/70* (2018.01)

(52) U.S. Cl.
CPC ............. *G06F 40/20* (2020.01); *G16H 10/60* (2018.01); *G16H 50/20* (2018.01); *G16H 50/70* (2018.01)

(58) Field of Classification Search
CPC ........ G06F 40/20; G16H 10/60; G16H 50/20; G16H 50/70
USPC .......................................................... 704/9
See application file for complete search history.

(56) References Cited

U.S. PATENT DOCUMENTS

| | | | | |
|---|---|---|---|---|
| 2002/0022956 A1* | 2/2002 | Ukrainczyk | ............ | G06F 40/20 |
| | | | | 707/E17.084 |
| 2020/0193153 A1* | 6/2020 | Lee | ........................ | G06F 40/226 |
| 2021/0183498 A1* | 6/2021 | Kalafut | .................... | G06T 11/60 |
| 2022/0012431 A1* | 1/2022 | Turkkan | ................ | G06F 40/205 |
| 2023/0132261 A1* | 4/2023 | Bulatov | ........... | G06V 30/19013 |
| | | | | 382/118 |

(Continued)

FOREIGN PATENT DOCUMENTS

| | | | | |
|---|---|---|---|---|
| CN | 115719058 A | * | 2/2023 | |
| CN | 119167114 A | * | 12/2024 | ............. G06N 3/048 |

(Continued)

OTHER PUBLICATIONS

Maddugoda, Chamathka. "A comprehensive review: Detection techniques for human-generated and AI-generated texts." (2023).*

(Continued)

*Primary Examiner* — Edwin S Leland, III
(74) *Attorney, Agent, or Firm* — Vincent Duffy; Joseph Kolodka

(57) ABSTRACT

Systems and methods for detecting artificial intelligence (AI) generated text. A candidate text can be truncated to obtain a prefix text and a remainder text by employing a truncation module. Regenerated model texts can be regenerated by utilizing the prefix text by employing an AI text generation model. Detection results can be predicted by comparing n-gram similarities of the regenerated model texts and the remainder text. The candidate text can be distinguished as AI generated text by providing explanation texts based on the detection results.

20 Claims, 8 Drawing Sheets

100

Truncating a candidate text to obtain a prefix text and a remainder text by employing a truncation module - 110

Obtaining regenerated model texts by utilizing the prefix text by employing an artificial intelligence (AI) text generation model - 120

Predicting detection results based on the responses by comparing n-gram similarities of the regenerated model texts and the remainder text by employing a detection module - 130

Distinguishing whether the candidate text is AI generated by providing explanation texts based on the detection results - 140

(56)　　　　　　References Cited

U.S. PATENT DOCUMENTS

| | | | | |
|---|---|---|---|---|
| 2024/0304329 A1* | 9/2024 | Cheng | .................... | G06F 40/40 |
| 2024/0378380 A1* | 11/2024 | Cheng | .................... | G16H 10/60 |
| 2024/0378870 A1* | 11/2024 | Cheng | ................. | G06V 10/454 |
| 2024/0419801 A1* | 12/2024 | Cheng | .................... | G06N 7/01 |

FOREIGN PATENT DOCUMENTS

| | | | | | | |
|---|---|---|---|---|---|---|
| CN | 119066182 B | * | 4/2025 | .............. | | G06N 5/04 |
| CN | 120124609 A | * | 6/2025 | ............ | | G06T 11/60 |
| CN | 120146041 A | * | 6/2025 | .............. | | G06N 5/04 |
| JP | 7554308 B1 | * | 9/2024 | | | |
| KR | 20230050671 A | * | 4/2023 | ........... | | G06F 40/284 |
| KR | 102547402 B1 | * | 6/2023 | .......... | | G06F 40/194 |
| WO | WO-2024233444 A1 | * | 11/2024 | ............. | | G16H 50/20 |

OTHER PUBLICATIONS

Mitchell, E., Lee, Y., Khazatsky, A., Manning, C. D., & Finn, C. (Jul. 23, 2023). Detectgpt: Zero-shot machine-generated text detection using probability curvature. In International Conference on Machine Learning (pp. 24950-24962). PMLR.

Yang, X., Cheng, W., Petzold, L., Wang, W. Y., & Chen, H. (May 27, 2023). Dna-gpt: Divergent n-gram analysis for training-free detection of gpt-generated text. arXiv preprint arXiv:2305.17359.

* cited by examiner

<u>100</u>

Truncating a candidate text to obtain a prefix text and a remainder text by employing a truncation module - 110

Obtaining regenerated model texts by utilizing the prefix text by employing an artificial intelligence (AI) text generation model - 120

Predicting detection results based on the responses by comparing n-gram similarities of the regenerated model texts and the remainder text by employing a detection module - 130

Distinguishing whether the candidate text is AI generated by providing explanation texts based on the detection results - 140

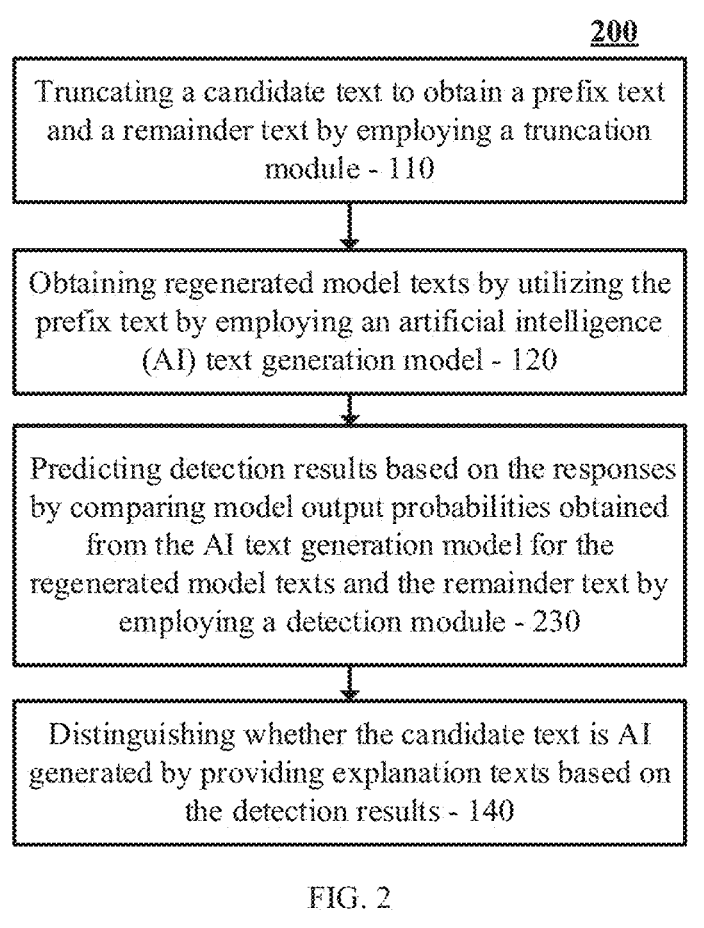

Truncating a candidate text to obtain a prefix text and a remainder text by employing a truncation module - 110

↓

Obtaining regenerated model texts by utilizing the prefix text by employing an artificial intelligence (AI) text generation model - 120

↓

Predicting detection results based on the responses by comparing model output probabilities obtained from the AI text generation model for the regenerated model texts and the remainder text by employing a detection module - 230

↓

Distinguishing whether the candidate text is AI generated by providing explanation texts based on the detection results - 140

FIG. 2

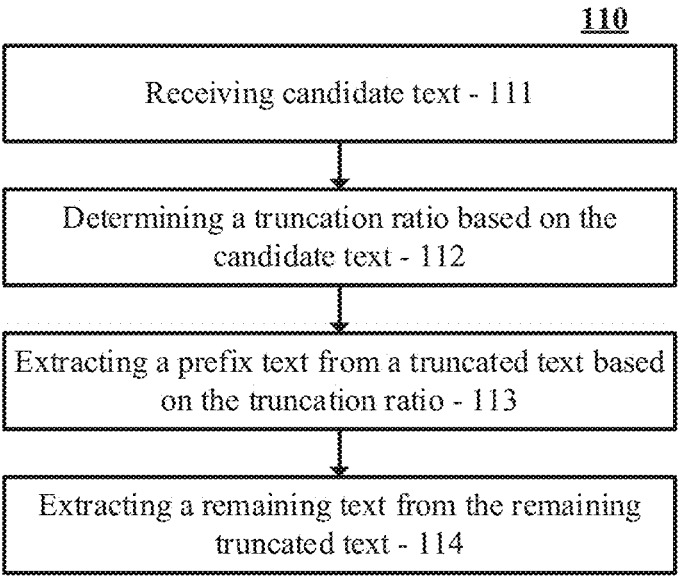

110

Receiving candidate text - 111

Determining a truncation ratio based on the candidate text - 112

Extracting a prefix text from a truncated text based on the truncation ratio - 113

Extracting a remaining text from the remaining truncated text - 114

FIG. 3

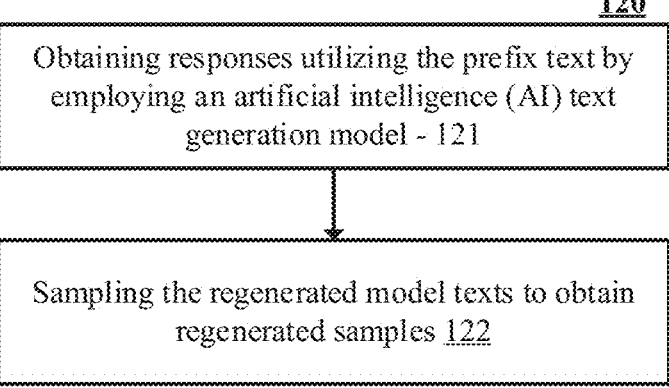

120

Obtaining responses utilizing the prefix text by employing an artificial intelligence (AI) text generation model - 121

Sampling the regenerated model texts to obtain regenerated samples 122

Obtaining model output probabilities ($p(Y \mid X)$) of the regenerated model texts and the prefix text - 231

Obtaining model output probability ($p(Y0 \mid X)$) of the remaining text and the prefix text - 232

Fitting the model output probabilities ($p(Y \mid X)$), and model output probability ($p(Y0 \mid X)$) into a detection equation to obtain detection score of the sequences - 233

Comparing the detection scores to a detection threshold to obtain detection results - 234

Obtaining responses and detection results for processing - 141

Fitting evidence result ($\varepsilon$) between responses and detection results into an evidence equation by employing the evidence module - 142

Providing explanation text by utilizing evidence results, regenerated model texts, and detection results - 143

FIG. 7

DETECTING ARTIFICIAL INTELLIGENCE GENERATED TEXT

RELATED APPLICATION INFORMATION

This application claims priority to U.S. Provisional App. No. 63/465,063 filed on May 9, 2023, incorporated herein by reference in its entirety.

BACKGROUND

Technical Field

The present invention relates to artificial intelligence model output analysis and more particularly, detecting artificial intelligence generated text.

Description of the Related Art

The remarkable progress in large pre-trained large language models (LLMs) has brought machine-generated text closer to human-written text in both fluency and diversity. However, this poses a pressing challenge for distinguishing the origin of the text whether it is machine generated or human created.

SUMMARY

According to an aspect of the present invention, a method is provided for detecting artificial intelligence (AI) generated text, by employing a processor device, including truncating a candidate text to obtain a prefix text and a remainder text by employing a truncation module, obtaining regenerated model texts by utilizing the prefix text by employing an AI text generation model, predicting detection results by comparing n-gram similarities of the regenerated model texts and the remainder text, and distinguishing whether the candidate text is AI generated by providing explanation texts based on the detection results.

According to another aspect of the present invention, a system is provided for detecting artificial intelligence (AI) generated text, including a memory, and one or more processors in communication with the memory configured to truncate a candidate text to obtain a prefix text and a remainder text by employing a truncation module, obtain regenerated model texts by utilizing the prefix text by employing an AI text generation model, predict detection results by comparing n-gram similarities of the regenerated model texts and the remainder text by employing a detection module, and distinguish whether the candidate text is AI generated by providing explanation texts based on the detection results.

According to yet another aspect of the present invention, a non-transitory computer program product including a computer-readable storage medium having program code for detecting artificial intelligence (AI) generated text wherein the program code when executed on a computer causes the computer to perform truncating a candidate text to obtain a prefix text and a remainder text by employing a truncation module, obtaining regenerated model texts by utilizing the prefix text by employing an AI text generation model, predicting detection results by comparing n-gram similarities of the regenerated model texts and the remainder text, and distinguishing whether the candidate text is AI generated by providing explanation texts based on the detection results.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a flow diagram illustrating a high-level overview of a method for detecting AI generated text by employing black box detection, in accordance with an embodiment of the present invention;

FIG. 2 is a flow diagram illustrating a high-level overview of a method for detecting AI generated text by employing white box detection, in accordance with an embodiment of the present invention;

FIG. 3 is a flow diagram illustrating a method for obtaining a prefix text from a truncated text extracted from a candidate text by employing a truncation module, in accordance with an embodiment of the present invention;

FIG. 4 is a flow diagram illustrating a method for obtaining regenerated model texts by utilizing the prefix text by employing an AI text generation model, in accordance with an embodiment of the present invention;

FIG. 6 is a flow diagram illustrating a method for predicting detection results based on the responses by comparing model output probabilities obtained from the AI text generation model for the regenerated model texts and the remainder text by employing a detection module, in accordance with an embodiment of the present invention;

FIG. 7 is a flow diagram illustrating a method for outputting explanation texts by employing an evidence module that utilizes the detection results, in accordance with an embodiment of the present invention;

DETAILED DESCRIPTION OF PREFERRED EMBODIMENTS

Figure 5:
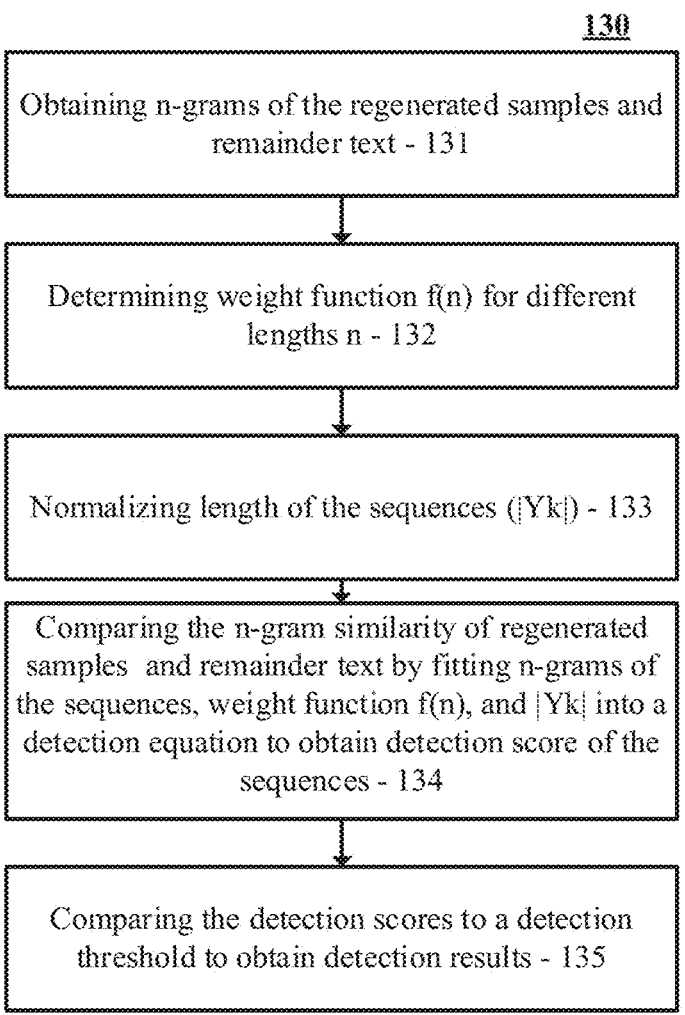
FIG. 5 is a flow diagram illustrating a method of predicting detection results based on the responses by comparing n-gram similarities of the regenerated model texts and the remainder text by employing a detection module, in accordance with an embodiment of the present invention.

In accordance with embodiments of the present invention, systems and methods are provided for detecting artificial intelligence generated text.

The present embodiments can distinguish AI-generated text with a training-free detection approach while providing explanations. In an embodiment, a candidate text can be truncated by an appropriate ratio to obtain a prefix text to regenerate model texts to compute and show a significant disparity between the human-generated and AI-generated two text types. In an embodiment, a black-box detection method can be employed where only the candidate text, prefix text and regenerated model texts can be obtained from the AI model. In another embodiment, a white-box detection method can be employed where model output probabilities of the prefix text and the regenerated model texts can be obtained for processing.

The release of ChatGPT™ and GPT-4™ by OpenAI™ led to a worldwide discussion about the efficient utilization of artificial intelligence (AI) assistant writing. Despite the fact that Large language models (LLMs) have achieved impressive success in natural language generation, many problems, such as fake news, and plagiarism in education, also arise. Scientific abstracts written by AI could fool scientists and lead to the disorder of human beliefs in science.

As AI-generated text gradually approaches human level, there is some fundamental difficulty in effectively detecting AI-generated text. This led to a recent debate of whether AI-generated text can be detected or not. However, there is still a lack of practical tests on AI-generated text detection, especially in the era of ChatGPT™.

Previous detection methods rely on the log its returned by the specific LLMs, like perturbation-based models or rank/ entropy-based approaches. But such detection tools fail when AI providers, such as OpenAI™, do not provide token log its. Because language models are not releasing model details to the public due to safety or competition reasons, detecting texts generated using language models also becomes more difficult. This scenario will only worsen as LLMs get actively updated and improved. Therefore, there is an urgent need to accurately detect AI-generated text to catch up with the rapid progress of LLMs.

Additionally, in the context of AI generated text detection, interpretability is especially important because it allows users to understand why a particular piece of content has been flagged or identified as potentially problematic. Without interpretability, a detection system may simply provide a "yes" or "no" answer without any explanation, leaving users to wonder why certain content was flagged, and others were not. This lack of transparency can lead to frustration and distrust in the system. Previous training-based methods are not flexible enough to adapt to new models and lack explanations.

The present embodiments can provide a general, interpretable, and easy-to-use detection method for LLMs.

The applications of detecting AI-generated texts are diverse and can be beneficial in various fields. Here are some common applications:

Fake News Detection: AI models can be used to generate realistic but false information. In an embodiment, fake news or misleading information can be identified and presented to a decision-making entity to be filtered out.

Content Moderation: Many online platforms rely on content moderation to ensure user safety and prevent the dissemination of harmful or inappropriate content. In another embodiment, AI-generated harmful or inappropriate content (e.g., hate speech, harassment, or spam) can be identified and presented to a decision-making entity to be removed.

Plagiarism Detection: In another embodiment, plagiarism using AI-generated text can be detected to help decision-making entities such as, educational institutions, publishers, and content creators maintain originality and uphold ethical standards.

Spam Filtering: AI models can generate convincing spam messages or phishing attempts. In another embodiment, spam filters can be improved by identifying and blocking AI-generated spam messages or phishing attempts.

Chatbot Validation: Many chatbots and virtual assistants employ AI models to generate responses. In another embodiment, responses provided by chatbots can be labeled as AI-generated and can be updated by a decision-making entity to ensure information is reliable and accurate.

Cybersecurity: In an embodiment, AI-generated texts that can be used in social engineering attacks or to create persuasive phishing emails can be detected which can aid a decision-making entity in identifying potential cybersecurity threats and preventing malicious activities.

Academics and Research: Researchers studying language models and their impact on society can use the present embodiments to identify and analyze the presence and influence of AI-generated texts in various domains.

Healthcare Provider Verification: Patients and healthcare professionals can interact through chats on a website, instant messaging, or through emails. Additionally, healthcare provider websites can employ chatbots to interact with patients. However, patients do not have the capability to determine whether the entity that they are entrusting their health data with is a human and not. In an embodiment, transparency can be provided by detecting whether the information provided by entity, whom the patient is interacting with, is not AI-generated which can alleviate stress and misinformation concerning health-related interactions. In another embodiment, decision-making entities, such as healthcare professionals, can verify and correct the detected AI generated text in healthcare records to better diagnose and treat their patients with correct information.

Referring now in detail to the figures in which like numerals represent the same or similar elements and initially to FIG. 1, a high-level overview of a method for detecting AI generated text by employing black box detection 100 is illustratively depicted in accordance with an embodiment of the present invention.

In an embodiment, a given candidate text 501 (shown in FIG. 8) can be distinguished whether it was generated by a certain language model like ChatGPT™ or a human. The candidate text 501 (shown in FIG. 8) can be extracted based on a truncation ratio to obtain a prefix text 531 (shown in FIG. 8). The prefix text 531 can be fed into the AI text generation model 521 (shown in FIG. 8) to obtain regenerated model texts 522 (shown in FIG. 8). A modified n-gram overlap ratio between the prefix text 531 and the regenerated model texts 522 can be employed to calculate a detection score 534 (shown in FIG. 8) and obtain detection results 526 (shown in FIG. 8). The detection score 534, prefix text 531, and the regenerated model texts 522 can be employed to generate explanation texts 537 (shown in FIG. 8). The candidate text 501 can be distinguished from AI-generated text by providing explanation texts 537 based on the detection results 526.

In block 110, a prefix text 531 can be extracted from a candidate text 501 by employing a truncation module 520.

In block 120, regenerated model texts 522 can be obtained by utilizing the prefix text 531 by employing an artificial intelligence text generation model 521.

In block 130, detection results 526 can be predicted based on the regenerated model texts 522 by employing a detection module 524 that compares n-gram similarities of the regenerated model texts 522 and the remainder text 532.

In block 140, the candidate text 501 can be distinguished as AI generated by providing explanation texts 537 based on the detection results 526.

Referring now to FIG. 2, a high-level overview of a method for detecting AI generated text by employing white box detection 200 is illustratively depicted in accordance with an embodiment of the present invention.

In another embodiment, a given candidate text 501 can be distinguished whether it was generated by a certain language model like ChatGPT™ or a human. The candidate text 501 can be extracted based on a truncation ratio to obtain a prefix text 531. The prefix text 531 can be fed into the AI text generation model 521 to obtain regenerated model texts Y1, . . . , Yk. Model output probabilities 523 can be obtained from the AI text generation model 521 to compute a detection score 534 and obtain detection results 526. The given candidate text 501 can be distinguished whether it was AI generated based on the detection results 526.

In block 110, a prefix text 531 can be extracted from a candidate text 501 by employing a truncation module 520.

In block 120, regenerated model texts 522 can be obtained by utilizing the prefix text 531 by employing an artificial intelligence text generation model 521.

In block 230, detection results 526 can be predicted based on the regenerated model texts 522 by comparing model output probabilities 523 obtained from the AI text generation model 521 for the regenerated model texts 522 and the remainder text 532 by employing a detection module 524.

In block 140, the candidate text 501 can be distinguished as AI generated by providing explanation texts 537 based on the detection results 526.

Referring now to FIG. 3, a method for obtaining a prefix text from a truncated text extracted from a candidate text by employing a truncation module 110 is illustrated, in accordance with an embodiment of the present invention.

In an embodiment, a prefix text 531 can be extracted from a candidate text 501 based on a truncation ratio. Given a sequence S=[Si, . . . , $S_L$], where L is the sequence length, a truncation ratio ($\lambda$) for splitting the sequence into two parts can be defined: X=[$S_1$, . . . , $S_{\lambda L}$], and $Y_0$=[$S_{\lambda+1}$, . . . , $S_L$].

In block 111, the candidate text 501 can be received for processing.

In block 112, a truncation ratio 502 can be determined based on the candidate text 501. The truncation ratio 502 is a hyperparameter that can be an element of [0, 1]. In an embodiment, the truncation ratio can be 0.5.

In block 113, a prefix text 531 can be extracted from the candidate text 501 according to the truncation ratio 502.

In block 114, a remainder text 532 can be extracted from the remainder of the truncated text.

Referring now to FIG. 4, a method for obtaining regenerated model texts by utilizing the prefix text by employing an AI text generation model (LLM) 120 is illustrated, in accordance with an embodiment of the present invention.

In an embodiment, regenerated model texts 522 can be obtained by employing an AI text generation model 521 and utilizing the prefix text 531. In an embodiment, the LLMs can be ChatGPT™, Google™ Bard™, Amazon™ Q, Meta AI™, etc. Other LLMs are contemplated.

In block 121, regenerated model texts 522 can be obtained by employing an AI text generation model (LLM) 521 and utilizing the prefix text 531. In an embodiment, the LLMs 521 can generate regenerated model texts 522 based on the prefix text (X) 531. The regenerated model texts 522 are denoted by $Y_k$=LLMs (X) where k is a number within sample size K.

In block 122, the regenerated model texts 522 can be sampled to obtain regenerated samples 503. In an embodiment, the regenerated model texts 522 are sampled K times, to get regenerated samples 503 as $\Omega$={$Y_1$, $Y_2$, . . . , $Y_K$}. In an embodiment, K can be 10. In another embodiment, K can be 5.

Referring now to FIG. 5, a method for predicting detection results based on the responses by comparing n-gram similarities of the regenerated model texts and the remainder text by employing a detection module 130 is illustrated, in accordance with an embodiment of the present invention.

Users can only access the model input and output through the application programming interfaces (API) of third-party providers such as Google™ and OpenAI™, without knowing the token probabilities and model weights of the generative text AI models employed.

In an embodiment, textual inputs and text output generated by the AI models can only be obtained. In the black-box scenario, the n-gram similarity of regenerated samples 503 and remainder text 532 can be compared to distinguish human and AI-generated text. Human generated remainder text will have much lower overlap with regenerated samples 503, compared to AI-generated text.

In block 131, sequence n-grams 504 can be obtained by employing the detection module 524. An n-gram is a sequence of n adjacent symbols or words in a particular order.

In block 132, a weight function $f(n)$ can be determined for different lengths n.

In block 133, the length of sequences can be normalized and can be represented by |Y| where Y is a sequence.

In block 134, the sequence n-grams, weight function $f(n)$ and normalized length of sequence |Y| can be fitted into a detection score equation 530 to obtain detection scores of the sequences by comparing the n-gram similarity of regenerated samples 503 and remainder text 532. The black box detection score equation 530 can be:

$$BScore = \frac{1}{K}\sum_{k=1}^{K}\sum_{n=n_0}^{N} f(n)\frac{|\text{grams}(Y_k, n) \cap \text{grams}(Y_0, n)|}{|Y_k||\text{grams}(Y_0, n)|},$$

where grams(Y, n) denotes a set of all sequence n-grams 504 in sequence Y, Y includes sequences of remainder text 532 $Y_0$ and sequences of regenerated model text 522 $Y_k$, k is an element of sample size K is, N is a number of sequences, $f(n)$ is an empirically chosen weight function for different lengths n, and |$Y_k$| is a normalized length of sequence $Y_k$ used to normalize grams ($Y_0$, n). In an embodiment, $f(n)$ can be n log(n), $n_0$=4, and N=25.

In block 135, the detection scores 534 are compared against a detection threshold 540 to obtain detection results 526. The detection threshold 540 can be computed by balancing the true positive rate (TPR) and the false positive rate (FPR). In an embodiment, the area under the receiver operating curve (AUROC) can be employed to emulate all different thresholds to calculate the TPR and FPR. In another embodiment, the TPR can be computed by fixing the FPR to 1%. The detection threshold 540 can be a hyperparameter that can be set based on the goals of the detection. If the goal is to increase precision, the detection threshold 540 can be small. If the goal is to increase recall, the detection threshold 540 can be high. In an embodiment, the detection threshold can be 0.95.

Referring now to FIG. 6, a method for predicting detection results based on the responses by comparing model output probabilities obtained from the AI text generation model for the regenerated model texts and the remainder text by employing a detection module 230 is illustrated, in accordance with an embodiment of the present invention.

In an embodiment that can employ white-box detection, model output probabilities 523 of the sequence Y and the prefix text 531 (X) can denoted by p(Y|X) which can be obtained from the AI Text Generation Model 521.

In block 231, the model output probabilities 523 of the input sequences and the generated tokens can be obtained from the LLMs 521.

In block 232, the model output probability 523 of the remainder text 532 sequence and the prefix text 531 can also be obtained from the LLMs 521.

In block 233, the model output probabilities 523 (p(Y|X)) for sequence Y and prefix text X, including p(Y_k|X) for sequence $Y_k$ and prefix text 531 (X), and model output probability 523 (p(Y_0|X)) can be fitted into detection score equation 530 to obtain detection scores 534 (Wscore) of the sequences. The white box detection equation 530 can be $$Wscore = \frac{1}{N}\sum\nolimits_{k=1}^{K} \log\frac{p(Y_0\,|\,X)}{p(Y_k\,|\,X)},$$

where p(Y_0|X) is model output probability of remainder text sequence $Y_0$ and prefix text X; p(Y_k|X) is model output probability of regenerated model text sequence $Y_k$ and prefix text X; k is a number within sample size K; N is a number of sequences.

In block 234, the detection scores 534 can be compared against a detection threshold 540 to obtain detection results 526. The detection threshold 540 can be computed by balancing the true positive rate (TPR) and the false positive rate (FPR). In an embodiment, the area under the receiver operating curve (AUROC) can be employed to emulate all different thresholds 540 to calculate the TPR and FPR. In another embodiment, the TPR can be computed by fixing the FPR to 1%. The detection threshold 540 can be a hyperparameter that can be set based on the goals of the detection. If the goal is to increase precision, the detection threshold 540 can be small. If the goal is to increase recall, the detection threshold 540 can be high. In an embodiment, the detection threshold 540 can be 0.95.

Referring now to FIG. 7, a method for outputting explanation texts by employing an evidence module that utilizes the detection results 140 is illustrated, in accordance with an embodiment of the present invention.

In an embodiment, evidence results 536 can include explanation texts 537 that can be provided to a decision-making entity 560 based on the detection results 526. The present embodiments can define the evidence result 536 (ε) as an overlapped sentence-piece comparison between each re-generated text in regenerated samples 503 (Ω) and remainder text 532 (Y_0).

In block 141, regenerated model texts 522 and detection results 526 can be obtained for processing.

In block 142, evidence result 536 between regenerated model texts 522 and detection results 526 can be fitted into an evidence equation 505 to compute evidence result by employing the evidence module. The evidence equation can be:

$$\varepsilon = \bigcup\nolimits_{k=1}^{K} (\mathrm{grams}(Y_k,\,n) \cap \mathrm{grams}(Y_0,\,n));$$

where k is an element of sample size K, grams ($Y_k$, n) is the sequence n-grams 504 $Y_k$, grams (Y_0, n) is the sequence n-grams 504 $Y_0$, and U is a union operator.

In block 143, explanation texts 537 can be provided by utilizing the evidence results 536, regenerated model texts 522 and detection results 526.

When n is large for n-gram overlap, the sentence pieces serve as strong evidence for AI-generated text since humans tend to write different text. However, even though the overlap is large, the evidence can be used flexibly by a decision-making entity 560 to alleviate issues with the possibility of misclassification.

Figure 8:
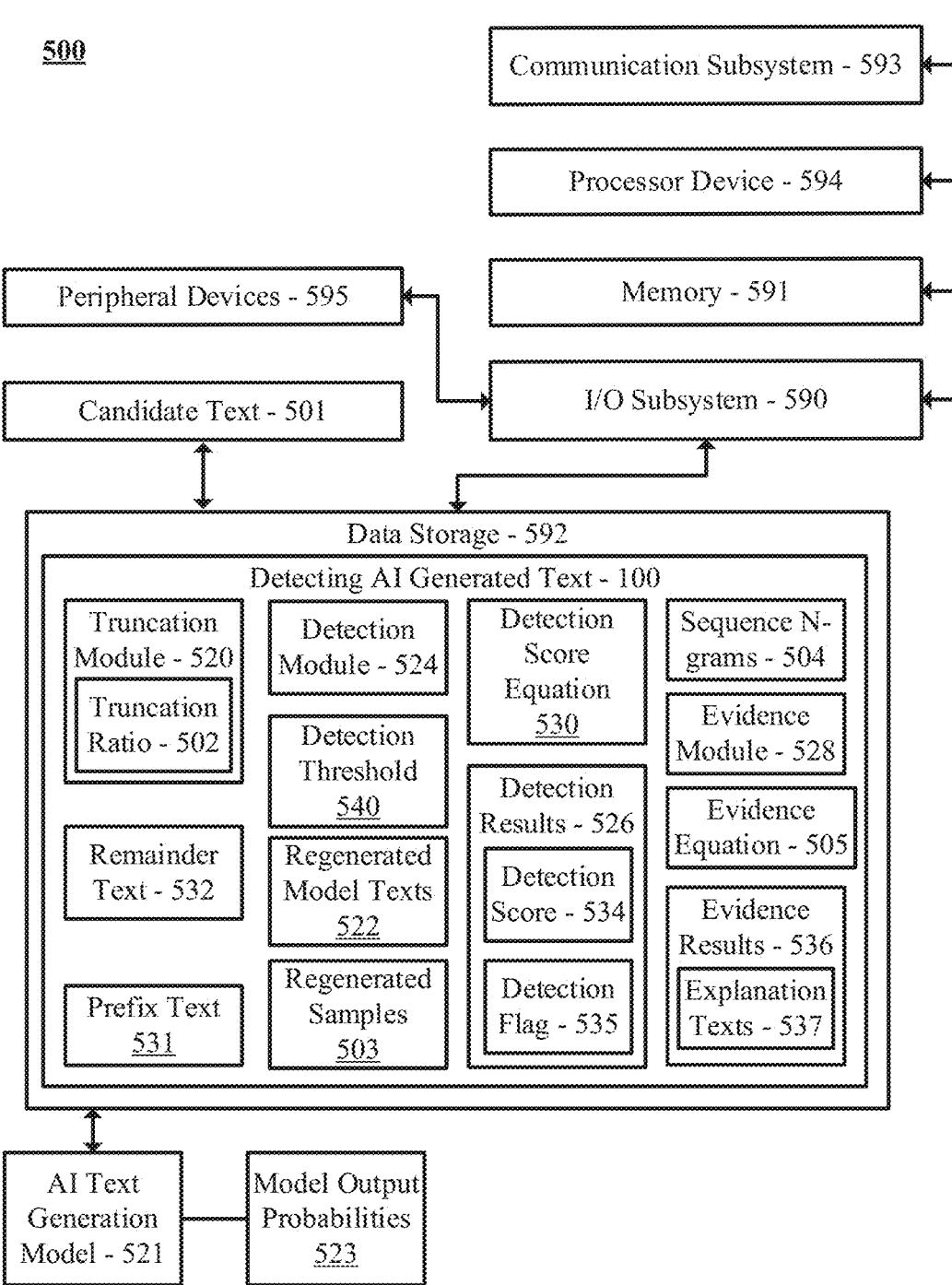
FIG. 8 is a block diagram illustrating a system for detecting AI generated text, in accordance with an embodiment of the present invention.

Referring now to FIG. 8, a block diagram illustrating a system for detecting AI generated text 500, in accordance with an embodiment of the present invention.

The computing device 500 illustratively includes the processor device 594, an input/output (I/O) subsystem 590, a memory 591, a data storage device 592, and a communication subsystem 593, and/or other components and devices commonly found in a server or similar computing device. The computing device 500 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 591, or portions thereof, may be incorporated in the processor device 594 in some embodiments.

The processor device 594 may be embodied as any type of processor capable of performing the functions described herein. The processor device 594 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 591 may be embodied as any type of volatile or non-volatile memory or data storage capable of performing the functions described herein. In operation, the memory 591 may store various data and software employed during operation of the computing device 500, such as operating systems, applications, programs, libraries, and drivers. The memory 591 is communicatively coupled to the processor device 594 via the I/O subsystem 590, which may be embodied as circuitry and/or components to facilitate input/output operations with the processor device 594, the memory 591, and other components of the computing device 500. For example, the I/O subsystem 590 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 590 may form a portion of a system-on-a-chip (SOC) and be incorporated, along with the processor device 594, the memory 591, and other components of the computing device 500, on a single integrated circuit chip.

The data storage device 592 may be embodied as any type of device or devices configured for short-term or long-term storage of data such as, for example, memory devices and circuits, memory cards, hard disk drives, solid state drives, or other data storage devices. The data storage device 592 can store program code for detecting AI generated text 100, including truncation module 520, detection module 524, and evidence module 528. Any or all of these program code blocks may be included in a given computing system.

In an embodiment, the truncation module 520 can be employed to determine the truncation ratio 502 to extract prefix text 531 and remainder text 532 from a candidate text 501. The AI Text Generation Model 521 can be employed to obtain regenerated model texts 522 and regenerated samples 503. The detection module 524 can be employed to determine the detection threshold 540 to fit the sequence N-grams 504, the regenerated samples 503 into a detection score equation 530 to obtain detection results 526 including a detection score 534 and a detection flag 535 (e.g., binary classification of candidate text 501). The evidence module 528 can be employed to fit the detection results 526, the regenerated model texts 522 into the evidence equation 505 to obtain evidence results 536 including explanation texts 537.

In another embodiment, the truncation module 520 can be employed to determine the truncation ratio 502 to extract prefix text 531 and remainder text 532 from a candidate text 501. The AI Text Generation Model 521 can be employed to obtain model output probabilities 523 of regenerated model texts 522 and the remainder text 532. The detection module 524 can be employed to determine the detection threshold 540 to fit the model output probabilities 523 into a detection score equation 530 to obtain detection results 526 including a detection score 534 and a detection flag 535 (e.g., binary classification of candidate text 501).

The communication subsystem 593 of the computing device 500 may be embodied as any network interface controller or other communication circuit, device, or collection thereof, capable of enabling communications between the computing device 500 and other remote devices over a network. The communication subsystem 593 may be configured to employ any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 500 may also include one or more peripheral devices 592. The peripheral devices 592 may include any number of additional input/output devices, interface devices, and/or other peripheral devices. For example, in some embodiments, the peripheral devices 592 may include a display, touch screen, graphics circuitry, keyboard, mouse, speaker system, microphone, network interface, and/or other input/output devices, interface devices, GPS, camera, and/or other peripheral devices.

Of course, the computing device 500 may also include other elements (not shown), as readily contemplated by one of skill in the art, as well as omit certain elements. For example, various other sensors, input devices, and/or output devices can be included in computing device 500, depending upon the particular implementation of the same, as readily understood by one of ordinary skill in the art. For example, various types of wireless and/or wired input and/or output devices can be employed. Moreover, additional processors, controllers, memories, and so forth, in various configurations can also be utilized. These and other variations of the processing system 500 are readily contemplated by one of ordinary skill in the art given the teachings of the present invention provided herein.

Figure 9:
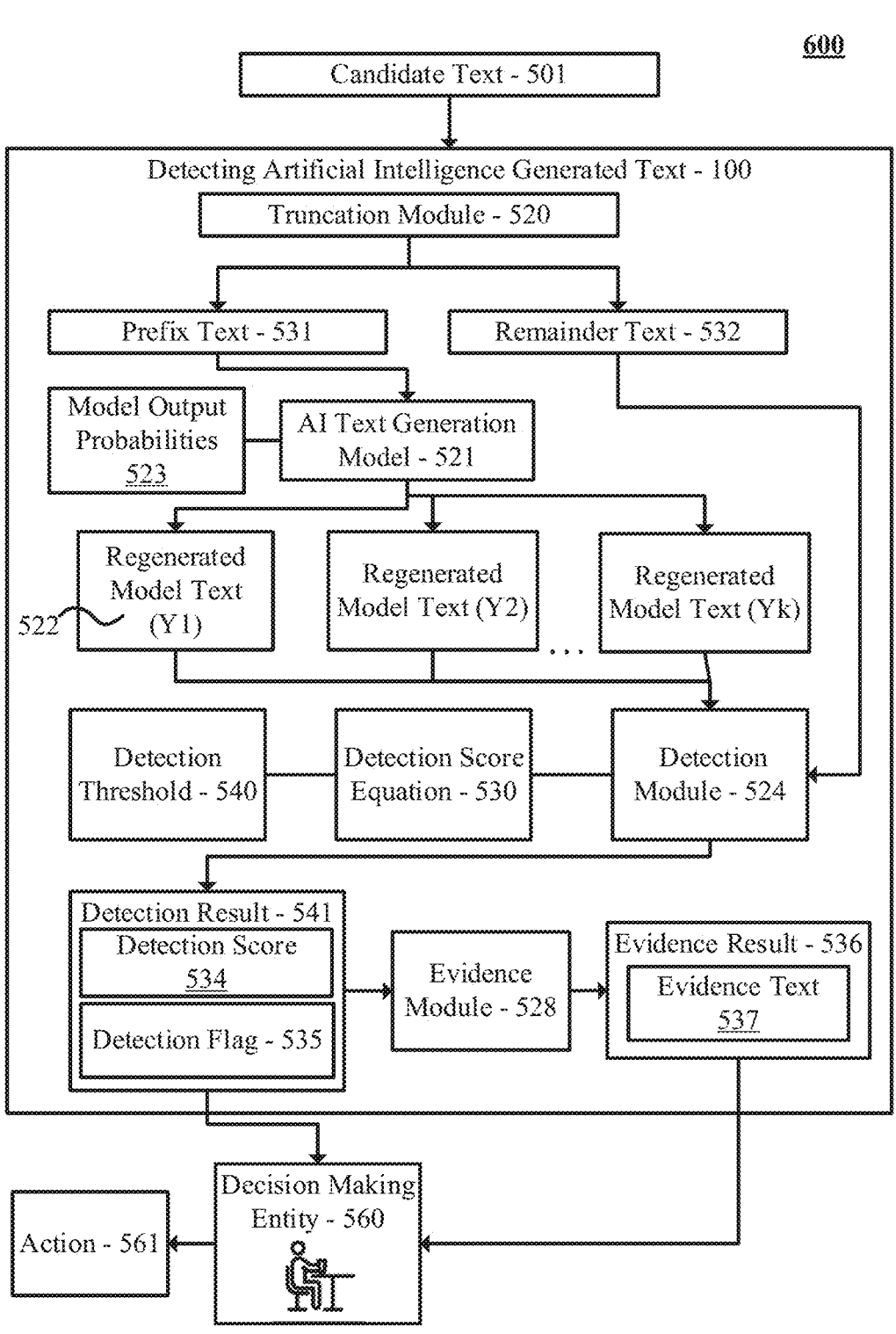
FIG. 9 is a block diagram illustrating a system for detecting AI generated text employing black box detection, in accordance with an embodiment of the present invention.

Referring now to FIG. 9, showing a system for detecting AI generated text 600 employing black box detection, in accordance with an embodiment of the present invention.

A decision-making entity 560 inputs a candidate text 502 to be processed. Candidate text 502 can be obtained from a query result input. For example, the query can be "Do mitochondria play a role in remodeling lace plant leaves during programmed cell death?" The candidate text 502, which is the query answer, can be "Yes, mitochondria play a role in programmed cell death by releasing molecules such as reactive oxygen species (ROS) and calcium ions which can trigger the degradation of cellular components and ultimately the death of the cell. This process is known as apoptosis and it is important for remodeling lace plant leaves during programmed cell death."

A prefix text 531 can be "Yes, mitochondria play a role in programmed cell death by releasing molecules such as reactive oxygen species (ROS) and calcium ions which can trigger the degradation of cellular components."

A remainder text 532 can be "and ultimately the death of the cell. This process is known as apoptosis and it is important for remodeling lacye plant leaves during programmed cell death."

The prefix text 531 can be inputted into the AI Text Generation Model 521 to regenerate query results and obtain regenerated model texts 522 including regenerated text 522 (Y1), regenerated text 522 (Y2) and regenerated text 522 (Yk). Regenerated text 522 (Y1) corresponds to the regenerated text 522 for sequence Y1. For example, regenerated text 522 (Y1) can be "This process is known as apoptosis and it is important for remodeling lace plant leaves during programmed cell death." Regenerated text 522 (Y2) corresponds to the regenerated text 522 for sequence Y2. Regenerated text 522 (Y2) can be "The apoptosis is known for this process, and it is important for remodeling lace plant leaves during programmed cell death." Regenerated text 522 (Yk) corresponds to the regenerated text 522 for sequence Yk. Regenerated text 522 (Yk) can be "The apoptosis is known for this process and it is essential for remodeling lace plant leaves during programmed cell death."

The regenerated model texts 522, the remainder text 532 can be inputted into the detection module 524 and fitted into the detection score equation 530, to compute detection score 534.

In an embodiment, the detection score equation 530 can be the black box score equation. In this embodiment, the detection score 534 can be the black box score (Bscore).

In another embodiment, the detection score equation 530 can be the white box score equation. In this embodiment, the detection score 534 is the white box score (Wscore), and the model output probabilities 523 can be utilized by the detection module 524. The detection score 534 can be compared against the detection threshold 540 to obtain detection flag 535 that shows whether candidate text 502 is AI generated or not. The detection score 534 and detection flag 535 are included in the detection result 541.

The detection result 541 can be inputted in the evidence module 528 to compute corresponding evidence results 536 including evidence text 537. The evidence texts 537 can be formatted to show the sequences that are classified as AI generated. The formatting can be simple text formats such as bolding, italicizing, underlining, changing the font color, etc. In the example above, evidence text 537 of candidate text 502 can be formatted as "Yes, mitochondria play a role in programmed cell death by releasing molecules such as reactive oxygen species (ROS) and calcium ions which can trigger the degradation of cellular components and ultimately the death of the cell. This process is known as apoptosis and it is important for remodeling lace plant leaves during programmed cell death." where the underlining serves as visual cues of the detected AI generated text. The evidence result 536 can then be utilized by the decision-making entity 560 to execute an action 561 based on the use case.

In an embodiment, for fake news detection, the action 561 can be that the decision-making entity 560 can flag a candidate text taken from text purporting to state the news as "fake news" after fact checking the candidate text 502. In another embodiment, for content moderation, the decision-making entity 560 can flag the candidate text 502 hate speech, harassment, or spam and remove candidate text 502. In another embodiment, for plagiarism detection, the action 561 can be that the decision-making entity 560 can flag the candidate text 502 as plagiarized and provide punitive actions. For spam filtering, the action 561 can be that the decision-making entity 560 can add the candidate text 502 to the blocked content list of the spam filter.

In an embodiment, for healthcare provider verification, the action 561 can be that the decision-making entity 560, as the patient, can accept the candidate text 502 as credible information and follow the recommendations concerning the candidate text 502. For a decision-making entity 560 as the health care provider, the action 561 can be that the decision-making entity 560 can modify the candidate text 502 to conform with proper health information and recommendations concerning a patient's healthcare.

In another embodiment, a healthcare record can be used as a candidate text 502. In this embodiment, a sequence within the healthcare record can be labeled as AI generated. A decision-making entity 560 can be presented with the healthcare record that has been labeled AI generated text to be updated. The healthcare record can then be updated based on the action 561 by the decision-making entity 560.

The present embodiments can employ neural networks, such as the AI text generation model 521 to regenerate texts for detecting AI generated text.

A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the inputted data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

Figure 10:
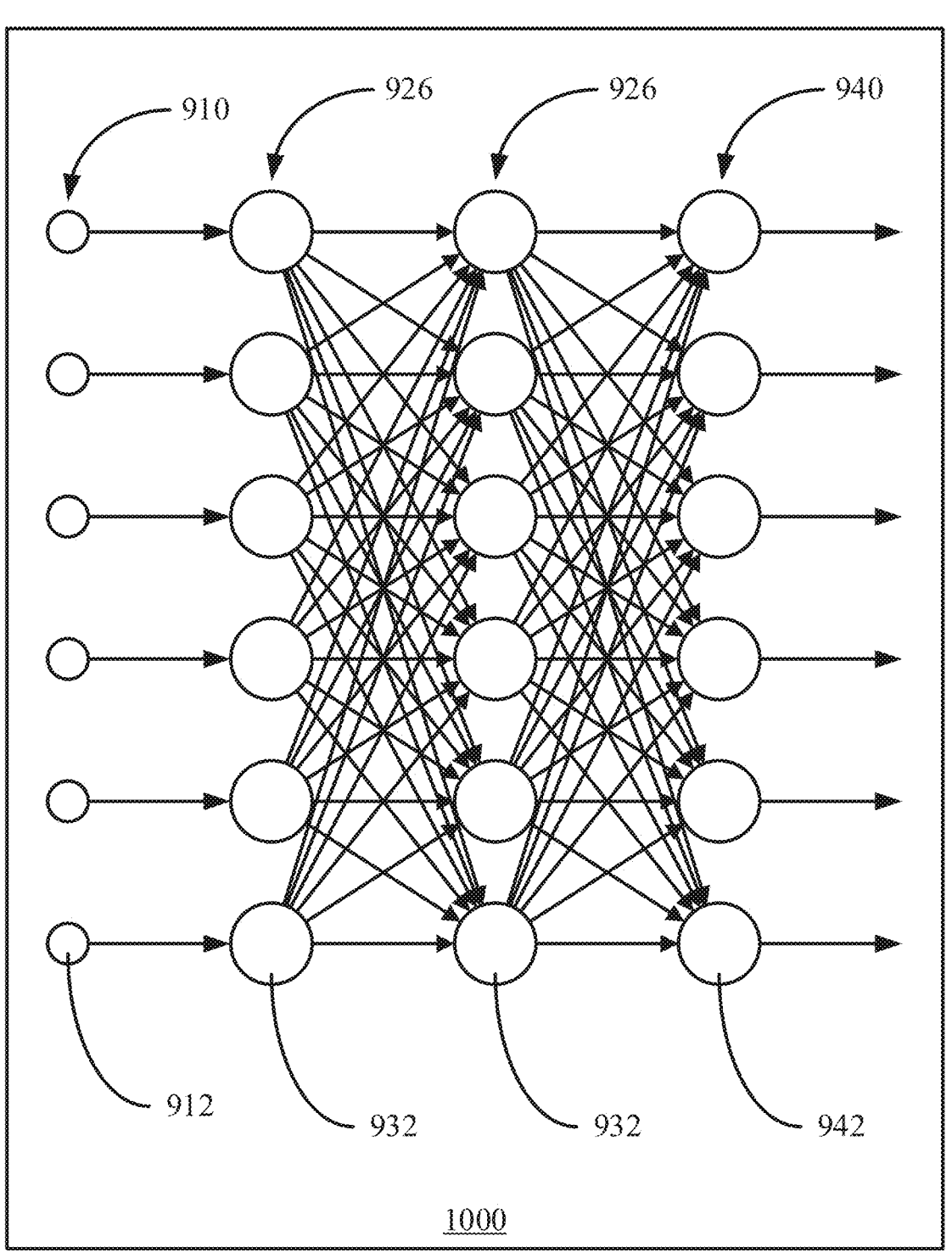
FIG. 10 is a block diagram illustrating a deep neural network system, in accordance with an embodiment of the present invention.

In FIG. 10, a deep neural network is shown. The deep neural network 1000, such as a multilayer perceptron, can have an input layer 911 of source nodes 912, one or more computation layer(s) 926 having one or more computation nodes 932, and an output layer 940, where there is a single output node 942 for each possible category into which the input example could be classified. An input layer 911 can have a number of source nodes 912 equal to the number of data values 912 in the input data 911. The computation nodes 932 in the computation layer(s) 926 can also be referred to as hidden layers, because they are between the source nodes 912 and output node(s) 942 and are not directly observed. Each node 932, 942 in a computation layer generates a linear combination of weighted values from the values output from the nodes in a previous layer, and applies a non-linear activation function that is differentiable over the range of the linear combination. The weights applied to the value from each previous node can be denoted, for example, by $w_1$, $w_2$, . . . $w_{n-1}$, $w_n$. The output layer provides the overall response of the network to the inputted data. A deep neural network can be fully connected, where each node in a computational layer is connected to all other nodes in the previous layer, or may have other configurations of connections between layers. If links between nodes are missing, the network is referred to as partially connected.

In an embodiment, the computation layers 926 can generate series of sequences based on a candidate text, and the context and syntax of the candidate text 501. The output layer can then provide the overall response of the network to the candidate text 501 as a regenerated model text 522. In another embodiment, the computation layers 926 can generate probability weights of the regenerated model texts 522 sequences based on the candidate text 501. The output layer can then provide the overall response of the network to the candidate text 501 as a regenerated model text 522 and a model output probability 523.

Training a deep neural network can involve two phases, a forward phase where the weights of each node are fixed and the input propagates through the network, and a backwards phase where an error value is propagated backwards through the network and weight values are updated.

The computation nodes 932 in the one or more computation (hidden) layer(s) 926 perform a nonlinear transformation on the input data 912 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for detecting artificial intelligence (AI) generated text, by employing a processor device, comprising:
    truncating a candidate text to obtain a prefix text and a remainder text by employing a truncation module;
    obtaining regenerated model texts by utilizing the prefix text by employing an AI text generation model;
    predicting detection results by comparing n-gram similarities of the regenerated model texts and the remainder text; and
    distinguishing whether the candidate text is AI generated by providing explanation texts based on the detection results.

2. The computer-implemented method of claim 1, further comprising labeling that a candidate text in a healthcare record is distinguished as AI generated to present to a decision-making entity.

3. The computer-implemented method of claim 2, further comprising updating the healthcare record with a candidate text distinguished as AI generated.

4. The computer-implemented method of claim 1, wherein predicting detection results further comprises obtaining a detection flag showing whether the candidate text is AI generated.

5. The computer-implemented method of claim 1, wherein predicting detection results further comprises calculating a detection score with:

$$BScore = \frac{1}{K}\sum\nolimits_{k=1}^{K}\sum\nolimits_{n=n_0}^{N} f(n)\frac{|\text{grams}(Y_k, n) \cap \text{grams}(Y_0, n)|}{|Y_k||\text{grams}(Y_0, n)|}$$

where grams(Y, n) denotes a set of all n-grams in sequence Y, Y includes remainder text sequence $Y_0$ and regenerated model text sequence $Y_k$, k is an element of sample size K is, N is a number of sequences, $f(n)$ is an empirically chosen weight function for different lengths n, and $|Y_k|$ is a normalized length of sequence $Y_k$ used to normalize grams ($Y_0$, n).

6. The computer-implemented method of claim 1, wherein predicting detection results further comprises comparing model output probabilities obtained from the AI text generation model for the regenerated model texts and the remainder text.

7. The computer-implemented method of claim 6, wherein comparing the model output probabilities further comprises calculating a detection score with:

$$Wscore = \frac{1}{N}\sum\nolimits_{k=1}^{K} \log\frac{p(Y_0 \mid X)}{p(Y_k \mid X)}$$

where p($Y_0$|X) is model output probability of remainder text sequence $Y_0$ and prefix text X; p($Y_k$|X) is model output probability of regenerated model text sequence $Y_k$ and prefix text X; k is a number within sample size K; N is a number of sequences.

8. The computer-implemented method of claim 1, wherein outputting explanation texts further comprises computing evidence results ($\varepsilon$) between the regenerated model texts and the detection results by employing an evidence module by:

$$\varepsilon = \bigcup\nolimits_{k=1}^{K} (\text{grams}(Y_k, n) \cap \text{grams}(Y_0, n));$$

where k is a number within sample size K, grams ($Y_k$, n) is the n-grams in regenerated model text sequence $Y_k$, grams ($Y_0$, n) is the n-grams in remainder text sequence $Y_0$, and U is a union operator.

9. A system for detecting artificial intelligence (AI) generated text, comprising:

a memory; and one or more processors in communication with the memory configured to:

truncate a candidate text to obtain a prefix text and a remainder text by employing a truncation module;

obtaining regenerated model texts by utilizing the prefix text by employing an AI text generation model;

predict detection results by comparing n-gram similarities of the regenerated model texts and the remainder text by employing a detection module; and distinguish whether the candidate text is AI generated by providing explanation texts based on the detection results.

10. The system of claim 9, wherein truncating the prefix text further comprises determining a truncation ratio.

11. The system of claim 9, further comprising labeling a candidate text in a healthcare record distinguished as AI generated to present to a decision-making entity.

12. The system of claim 11, further comprising updating a healthcare record with a candidate text distinguished as AI generated.

13. The system of claim 9, wherein predicting detection results further comprises calculating a detection score with:

$$BScore = \frac{1}{K}\sum\nolimits_{k=1}^{K}\sum\nolimits_{n=n_0}^{N} f(n)\frac{|\text{grams}(Y_k, n) \cap \text{grams}(Y_0, n)|}{|Y_k||\text{grams}(Y_0, n)|}$$

where grams(Y, n) denotes a set of all n-grams in sequence Y, Y includes remainder text sequences $Y_0$ and regenerated model text sequence $Y_k$, k is an element of sample size K is, N is a number of sequences, $f(n)$ is an empirically chosen weight function for different lengths n, and $|Y_k|$ is a normalized length of sequence $Y_k$ used to normalize grams ($Y_0$, n).

14. The system of claim 9, wherein predicting detection results further comprises comparing model output probabilities obtained from the AI text generation model for the regenerated model texts and the remainder text.

15. The system of claim 14, wherein comparing the model output probabilities further comprises calculating a detection score with:

$$Wscore = \frac{1}{N}\sum\nolimits_{k=1}^{K} \log\frac{p(Y_0 \mid X)}{p(Y_k \mid X)}$$

where p($Y_0$|X) is a model output probability of remainder text sequence $Y_0$ and prefix text X; p($Y_k$|X) is model output probability of regenerated model text sequence $Y_k$ and prefix text X; k is a number within sample size K; N is a number of sequences.

16. The system of claim 9, wherein outputting explanation texts further comprises computing evidence results ($\varepsilon$) between the regenerated model texts and the detection results by employing an evidence module by:

$$\varepsilon = \bigcup\nolimits_{k=1}^{K} (\text{grams}(Y_k, n) \cap \text{grams}(Y_0, n))$$

where k is a number within sample size K, grams ($Y_k$, n) is the n-grams in regenerated model text sequence $Y_k$, grams ($Y_0$, n) is the n-grams in remainder text sequence $Y_0$, and U is a union operator.

17. A non-transitory computer program product comprising a computer-readable storage medium including program code for detecting artificial intelligence (AI) generated text wherein the program code when executed on a computer causes the computer to perform:

truncating a candidate text to obtain a prefix text and a remainder text by employing a truncation module;

obtaining regenerated model texts by utilizing the prefix text by employing an AI text generation model;

predicting detection results by comparing n-gram similarities of the regenerated model texts and the remainder text; and distinguishing whether the candidate text is AI generated by providing explanation texts based on the detection results.

18. The non-transitory computer program product of claim 17, wherein predicting detection results further comprises calculating a detection score with:

$$BScore = \frac{1}{K}\sum_{k=1}^{K}\sum_{n=n_0}^{N} f(n) \frac{|grams(Y_k, n) \cap grams(Y_0, n)|}{|Y_k||grams(Y_0, n)|}$$

where grams(Y, n) denotes a set of all n-grams in sequence Y, S includes sequences $Y_0$ and $Y_k$, k is an element of sample size K is, N is a number of sequences, $f(n)$ is an empirically chosen weight function for different lengths n, and $|Y_k|$ is a normalized length of sequence $Y_k$ used to normalize grams $(Y_0, n)$.

19. The non-transitory computer program product of claim 17, wherein predicting detection results further comprises comparing model output probabilities obtained from the AI text generation model for the regenerated model texts and the remainder text by calculating a detection score with:

$$Wscore = \frac{1}{N}\sum_{k=1}^{K} \log \frac{p(Y_0 \mid X)}{p(Y_k \mid X)}$$

where $p(Y_0|X)$ is model output probability of remainder text sequence $Y_0$ and prefix text X; $p(Y_k|X)$ is model output probability of regenerated model text sequence $Y_k$ and prefix text X; k is a number within sample size K; N is a number of sequences.

20. The non-transitory computer program product of claim 17, wherein outputting explanation texts further comprises computing evidence results ($\varepsilon$) between the regenerated model texts and the detection results by employing an evidence module by:

$$\varepsilon = \bigcup_{k=1}^{K} (grams(Y_k, n) \cap grams(Y_0, n))$$

where k is a number within sample size K, grams $(Y_k, n)$ is the n-grams in sequence $Y_k$, grams $(Y_0, n)$ is the n-grams in sequence $Y_0$, and U is a union operator.

\* \* \* \* \*